(12) United States Patent
Barry, Jr. et al.

(10) Patent No.: US 8,852,140 B2
(45) Date of Patent: Oct. 7, 2014

(54) SYSTEM AND METHOD FOR ADJUSTMENT OF BLOOD SEPARATION PROCEDURE PARAMETERS

(75) Inventors: John W. Barry, Jr., Mount Prospect, IL (US); Brian C. Case, Lake Villa, IL (US); Lan T. Nguyen, Vernon Hills, IL (US)

(73) Assignee: Fenwal, Inc., Lake Zurich, IL (US)

( * ) Notice: Subject to any disclaimer, the term of this patent is extended or adjusted under 35 U.S.C. 154(b) by 425 days.

(21) Appl. No.: 13/345,305

(22) Filed: Jan. 6, 2012

(65) Prior Publication Data
US 2012/0175313 A1 Jul. 12, 2012

Related U.S. Application Data

(60) Provisional application No. 61/432,002, filed on Jan. 12, 2011.

(51) Int. Cl.
| | |
|---|---|
| *B01D 17/12* | (2006.01) |
| *B01D 17/00* | (2006.01) |
| *B01D 43/00* | (2006.01) |
| *A61M 1/36* | (2006.01) |

(52) U.S. Cl.
CPC ........... *A61M 1/3693* (2013.01); *A61M 1/3672* (2013.01); *A61M 2202/0427* (2013.01)
USPC ............... 604/30; 210/86; 210/103; 210/134; 210/143; 210/252; 210/258; 210/739; 210/745; 604/4.01; 604/5.01; 604/6.01; 604/6.07; 604/6.11; 604/28

(58) Field of Classification Search
CPC .................. A61M 1/3693; A61M 2202/0427; A61M 1/3672; A61M 2205/3331; A61M 2205/3306
USPC .......... 210/696, 698, 739, 745, 86, 103, 134, 210/143, 252, 258; 604/4.01, 5.01, 6.01, 604/6.07, 6.11, 28, 30
See application file for complete search history.

(56) References Cited

U.S. PATENT DOCUMENTS 4,713,176 A * 12/1987 Schoendorfer et al. ....... 210/645
6,348,156 B1 2/2002 Vishnoi
(Continued)

FOREIGN PATENT DOCUMENTS

| EP | 0 416 808 A1 | 3/1991 |
|---|---|---|
| WO | WO 96/39209 A1 | 12/1996 |
| WO | WO 02/05059 A2 | 1/2002 |

OTHER PUBLICATIONS

Extended European Search Report for European Patent Appln. No. 12150642.2, dated Apr. 18, 2012.
(Continued)

*Primary Examiner* — John Kim
(74) *Attorney, Agent, or Firm* — Cook Alex Ltd.

(57) ABSTRACT

Systems and methods are provided for automatically adjusting the operational parameters of a blood separation procedure. A blood separation device has an inlet for passing fluid thereinto and an outlet for removing fluid therefrom. A pump system is provided for moving fluid into and out of the device. In use, blood is conveyed into the device, where platelets are separated from at least a portion of the blood. A controller determines the amount of platelets in the device. Based at least in part on the amount of platelets in the device, corrective action is taken to avoid platelet aggregation in the device. The corrective action may be conveying an elevated amount of anticoagulant into the blood and/or the device and may be initiated when the determined amount of platelets approaches, meets, or exceeds a threshold predicted likelihood of platelet aggregation.

22 Claims, 10 Drawing Sheets

(56) References Cited

U.S. PATENT DOCUMENTS

| | | |
|---|---|---|
| 6,875,191 B2 | 4/2005 | Smith et al. |
| 7,011,761 B2 | 3/2006 | Muller |
| 7,087,177 B2 | 8/2006 | Min |
| 7,297,272 B2 | 11/2007 | Min |
| 7,708,710 B2 | 5/2010 | Min |
| 8,075,468 B2 | 12/2011 | Min |

OTHER PUBLICATIONS

Kozek-Langenecker et al., "Perioperative Coagulation Monitoring," Balliere's Best Practice and Research, Clinical Anesthesiology, Balliere Tindall, London, US, vol. 24, No. 1, Mar. 1, 2010, pp. 27-40.

Gabbasov, Z.A. et al., "Platelet Aggregation: The Use of Optical Density Formation in Platelet Suspension," Thrombosis Research, Tarrytown, NY, US vol. 54, No. 3, May 1, 1989, pp. 215-223.

\* cited by examiner

SYSTEM AND METHOD FOR ADJUSTMENT OF BLOOD SEPARATION PROCEDURE PARAMETERS

This application claims priority from and the benefit of U.S. provisional patent application Ser. No. 61/432,002, filed Jan. 12, 2011, which is hereby incorporated herein by reference.

BACKGROUND

1. Field of the Disclosure

The present subject matter relates to systems and methods for processing and collecting blood, blood constituents, or other suspensions of cellular material. More particularly, the present subject matter relates to automatic control and adjustment of blood separation procedure parameters during processing.

2. Description of Related Art

Today it is routine to separate whole blood, usually by centrifugation, into its various therapeutic components, such as red blood cells, platelets, and plasma.

Conventional blood processing methods use durable centrifuge equipment in association with single use, sterile fluid circuits or processing systems, typically made of plastic. The operator installs a fresh, sterile disposable system in the centrifuge before processing and removes it afterwards and discards it.

With a disposable system loaded onto the centrifuge (or just prior to or during loading) the operator typically enters, for example, by means of a touch screen or other user interface system, a particular processing protocol to be executed by the system (e.g., a procedure wherein platelets are separated from whole blood and collected) and other parameters (e.g., the weight of the donor, the desired volume of separated blood component to be collected, etc.). When the system has been programmed, the operator phlebotomizes a donor and the system carries out the procedure, under the supervision of the operator.

During processing, events may occur that compromise the procedure or the quality of the separated and collected blood component(s). One common occurrence is platelet aggregation where, during platelet collection procedures, platelets begin to stick to each other and become aggregated in the centrifuge. Known systems and protocols are not adequately suited to diagnose and counteract or preemptively avoid such platelet aggregation. Some systems allow for operator intervention, but it can be difficult for an operator to diagnose and/or predict platelet aggregation and, even when the operator can do so, it may still be difficult to properly adjust the process parameters so as to avoid platelet aggregation. The need therefore exists for automated blood processing controllers that can automatically prevent platelet aggregation, without the need for operator intervention.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately as set forth in the claims appended hereto.

In one aspect, a blood processing method comprises conveying blood into a blood separation device and determining the amount of platelets in the blood and/or in the device. The likelihood of platelet aggregation in the blood separation device is predicted based at least in part on the determined amount of platelets. If the predicted likelihood of platelet aggregation approaches, meets, or exceeds a predetermined value, an operational parameter may be adjusted.

In another aspect, a blood separation system comprises a device adapted for separating a blood component from blood. The device includes an inlet for passing fluid thereinto and an outlet for removing fluid therefrom. The system further includes a pump system for moving fluid through the system, and a controller. The controller is configured, e.g. programmed, to actuate the pump system to convey blood into the device. The controller determines the amount of platelets in the blood and/or in the device and predicts the likelihood of platelet aggregation based at least in part on the determined amount of platelets. If the predicted likelihood of platelet aggregation in the devices approaches, meets, or exceeds a predetermined value, the controller may adjust the operation of the pump system.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

The present subject matter is described below, for purposes of illustration only and not limitation, in terms of how it could be incorporated into a device of the type marketed as the ALYX® blood processing systems by Fenwal, Inc. of Lake Zurich, Ill., which is described in greater detail in U.S. Pat. Nos. 6,348,156; 6,875,191; 7,011,761; 7,087,177; and 7,297,272 and U.S. Patent Application Publication No. 2005/0137516, all of which are hereby incorporated herein by reference. However, the present subject matter is not limited to a particular blood processing system and is also applicable to other blood separation systems such as the AMICUS® blood processing systems marketed by Fenwal, Inc. (as described in greater detail in U.S. Pat. No. 5,868,696, which is hereby incorporated herein by reference) and the Spectra and TRIMA® systems marketed by CaridianBCT, and the MCS® 9000 system marketed by Haemonetics Corporation.

Figure 1:
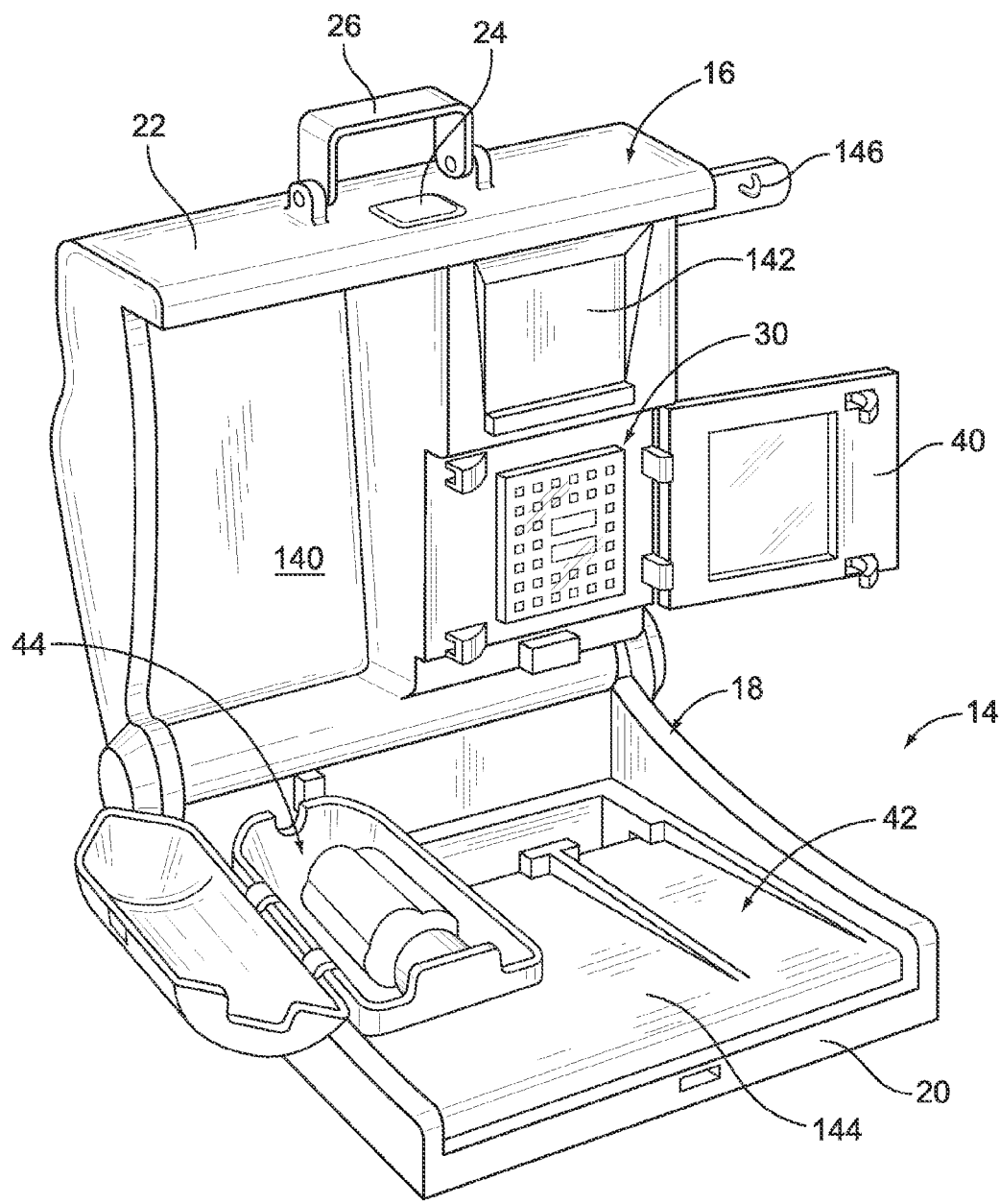
FIG. 1 is a perspective view of a processing device suitable for use with a blood or blood component processing system according to the present disclosure.
Figure 2:
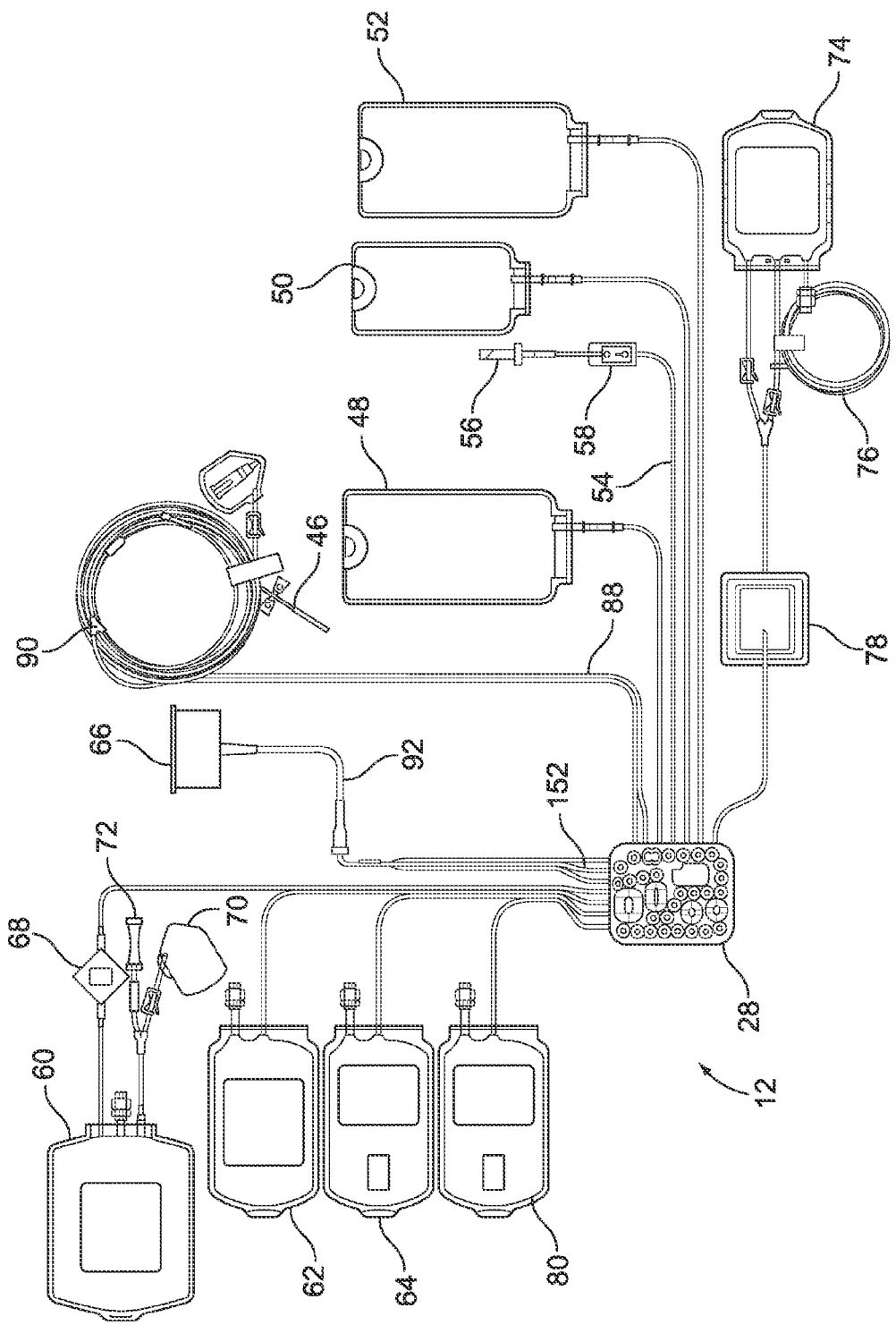
FIG. 2 is a schematic view of a disposable flow set suitable for use with the processing device shown in FIG. 1.

FIGS. 1 and 2 show components of a fluid processing system that embodies various aspects of the present subject matter. The system can be used for processing various fluids. The system is particularly well suited for processing whole blood and other suspensions of biological cellular materials and will be described in this context.

Generally speaking, the system includes three principal components. These are a blood processing device 14 (FIG. 1), a disposable liquid and blood flow set 12 (FIG. 2), and a controller 16 (FIG. 1) that governs the interaction between the flow set 12 and the blood processing device 14 to perform a blood processing and collection procedure selected by the operator.

I. The Durable Blood Processing Apparatus

The blood processing device 14 and controller 16 are intended to be durable items capable of long term use. In the illustrated embodiment, the blood processing device 14 and controller 16 are mounted inside a portable housing or case 18 (FIG. 1). The case 18 presents a compact footprint, suited for set up and operation upon a table top or other relatively small surface. The case 18 is also intended to be transported easily to a collection site.

The case 18 includes a base 20 and a hinged lid 22, which opens (as FIG. 1 shows) and closes. The lid 22 may include a latch 24 for releasably locking the lid 22 closed and a handle 26, which the operator can grasp for transporting the case 18 when the lid 22 is closed. In use, the base 20 is intended to rest on a generally horizontal support surface.

II. The Disposable Blood Processing Apparatus

As for the fluid circuit or flow set 12 (FIG. 2), it is intended to be a sterile, single use, disposable item. Before beginning a given blood processing and collection procedure, the operator loads various components of the flow set 12 in the case 18 in association with the device 14. The controller 16 implements the procedure based upon preset protocols, taking into account other input from the operator. Upon completing the procedure, the operator removes the flow set 12 from association with the device 14. The portions of the set 12 holding the collected blood component or components (e.g., collection containers or bags) are removed from the case 18 and retained for storage, transfusion, or further processing. The remainder of the set 12 is removed from the case 18 and discarded.

A. The Cassette

The various components of the set 12 are connected by flexible tubing to the ports of a fluid pressure-actuated cassette 28. The cassette 28 provides a centralized, programmable, integrated platform for all the pumping and valving functions required for a given blood processing procedure. In use, the cassette 28 is mounted to a pump and valve station 30 of the device 14. The pump and valve station 30 applies positive and negative pneumatic pressure to the cassette 28 to control and direct liquid flow therethrough.

Figure 3:
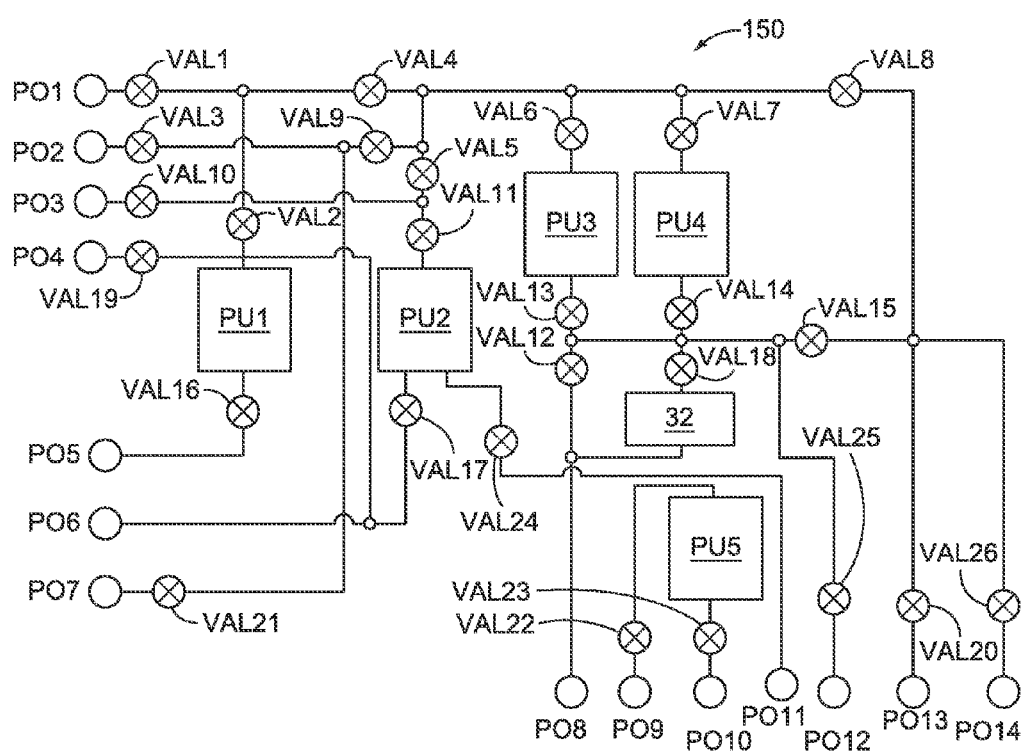
FIG. 3 is a schematic view of a blood processing circuit defined by a cassette of the flow set of FIG. 2, which can be programmed to perform a variety of different blood processing procedures in association with the device shown in FIG. 1.

The cassette 28 has an array of interior cavities formed on both its front and back sides. The interior cavities define the pumps, valve stations, and flow paths shown schematically in FIG. 3. The illustrated cassette 28 defines five pump stations PU1 to PU5. The first pump PU1 is an in-process pump, the second pump PU2 is a plasma pump, the third and fourth pumps PU3 and PU4 are donor pumps, and the fifth pump PU5 is an anticoagulant pump. The cassette 28 further defines in-line valves VAL1 to VAL26, which may be opened or closed to direct fluid through the cassette 28, via the interconnecting flow paths. An additional interior cavity 32 may be provided on the back side of the cassette 28 to form a station that holds a filter material for removing clots and cellular aggregations that can form during blood processing.

Flexible diaphragms overlie the front and back sides of the cassette 28 and localized applications of positive and negative fluid pressures upon the regions of the diaphragm overlaying the pump and valve stations serves to actuate them. These localized applications of positive and negative fluid pressures on the diaphragm regions overlaying the pump stations serve to expel liquid out of the pump stations (with application of positive pressure) and draw liquid into the pump stations (with application of negative pressure). Likewise, localized applications of positive and negative fluid pressure on the diaphragm regions overlaying the valves will serve to close and open them, respectively.

The cassette 28 includes a plurality of pre-molded ports PO1 to PO14 which extend out along two side edges of the cassette body. The cassette 28 is vertically mounted for use in the pump and valve station 30. The pump and valve station 30 has a door 40 that is hinged to move between an open position (FIG. 1) in which the cassette 28 may be loaded and unloaded, and a closed position in which the cassette 28 is retained within the pump and valve station 30 during a blood separation procedure. The operation of the pump and valve station 30 to control fluid flow through the cassette 28 can be understood with reference to U.S. Patent Application Publication No. 2009/0215602, which is hereby incorporated herein by reference.

The cassette 28 is mounted in the pump and valve station 30 with the ports PO8 to PO14 facing downward and the ports PO1 to PO7 vertically stacked one above the other and facing laterally. The ports PO8 to PO14, by facing downward, are oriented with container support trays 42 formed in the base 20. The ports PO1 to PO7, facing laterally, are oriented toward a centrifuge station 44 of the device 14. This ordered orientation of the ports provides a centralized, compact unit aligned with the operative regions of the case 18.

The individual ports PO1 to PO14 are connected to the other components of the set 12 by flexible tubing. In particular, the set 12 shown in FIG. 2 includes a vascular access member 46, such as a needle, an anticoagulant container 48, a red blood cell additive solution container 50, and a saline container 52. The disposable flow set 12 further includes tubing 54 leading to a connection device 56 (e.g., a spike in FIG. 2) for connection to a platelet storage solution container (not illustrated), if non-plasma platelet storage fluid is to be used. The illustrated tubing 54 includes an in-line sterility filter 58 of the type employed in a sub-micron filter, such as a 0.22 μm pore membrane filter, to prevent the passage of viruses or larger microbes, thereby preventing contamination and maintaining an effectively closed system. The disposable set 12 also includes a platelet collection container 60, a plasma collection container 62, and a red blood cell collection container 64 for collecting the blood components that are separated by a blood processing chamber 66 of the disposable set 12. The platelet collection container 60 is illustrated with an associated in-line leukoreduction filter 68, a gas exhaust or air burp bag 70 for removing an amount of gas from the collected platelets, and a sampling pack 72 for segregating an amount of the separated platelets for subsequent testing and/or tracking purposes according to known practice. A red blood cell storage container 74, including segmented tubing 76 (for segregating an amount of the separated red blood cells for subsequent testing and/or tracking purposes) and an in-line leukoreduction filter 78, is also included for post-separation storage of the red blood cells. The set 12 further includes an in-process container 80 for temporarily holding blood during a separation procedure. The functionality of the foregoing components will be described in greater detail in the context of an exemplary blood separation procedure.

Those having skill in the art will appreciate that each port of the cassette 28 may be associated with a variety of components and tasks, but in the illustrated embodiment, the first port PO1 is connected to the in-process container 80 by flexible tubing. The second port PO2 is connected to the red blood cell collection container 64 by tubing. The third port P03 is connected to the plasma collection container 62 by tubing. The fourth port PO4 is connected to the platelet collection container 60 by tubing. The fifth port PO5 is connected to a (whole blood) inlet 82 of the chamber 66 (FIG. 4) by tubing. The sixth port PO6 is connected to a first (plasma) outlet 84 of the chamber 66 by tubing. The seventh port PO7 is connected to a second (red blood cell) outlet 86 of the chamber 66 by tubing. The eighth port PO8 is connected to the vascular access member 46 by tubing. The ninth port P09 is associated with tubing 88 leading to a y-connector 90 for adding anticoagulant to whole blood from the blood source. The tenth port PO10 is associated with the anticoagulant container 48. The eleventh port PO11 is associated with the platelet storage solution container (not illustrated). The twelfth port PO12 is associated with the red blood cell additive solution container 50. The thirteenth port PO13 is associated with the saline container 52. The fourteenth port PO14 is associated with the red blood cell storage container 74.

The tubes extending from ports PO5, PO6, and PO7 to the chamber 66 are bundled together as an umbilicus 92. When installed in the processing station, the umbilicus 92 links the rotating processing chamber 66 with the cassette 28 without need for rotating seals, as will be described in greater detail herein.

B. The Blood Processing Chamber

Figure 4:
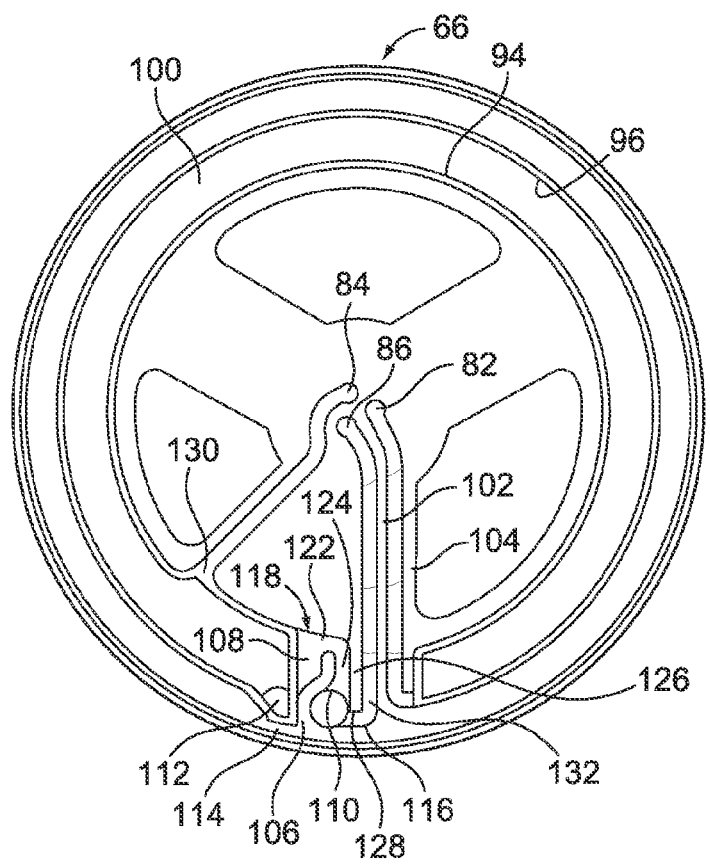
FIG. 4 is a top plan view of a blood processing chamber of the flow set shown in FIG. 2.
Figure 5:
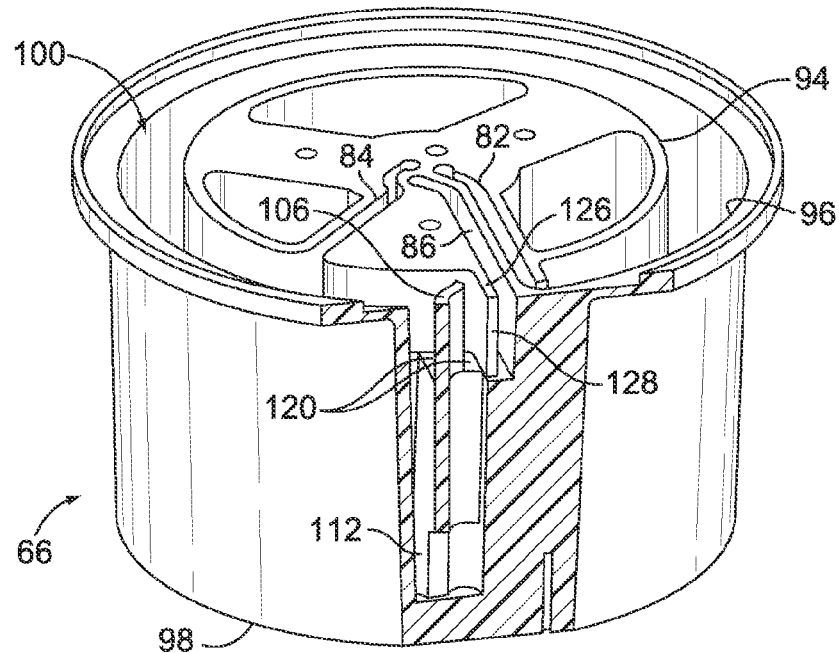
FIG. 5 is a perspective view of the blood processing chamber of FIG. 4, with a portion thereof cut away for illustrative purposes.
Figure 6:
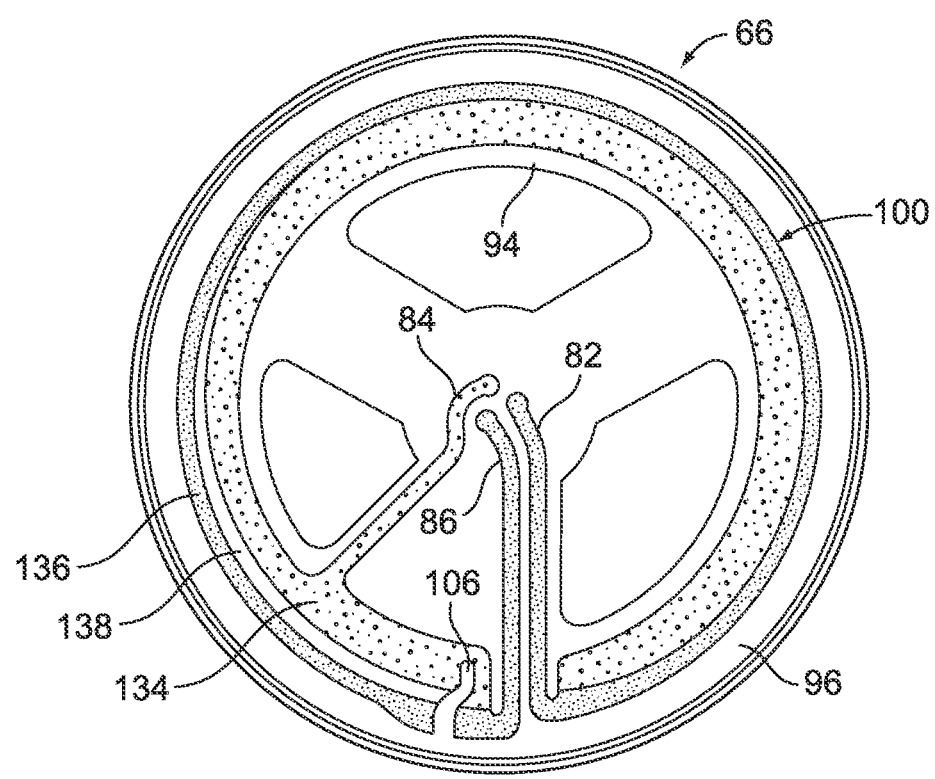
FIG. 6 is a top plan view of the blood processing chamber of FIG. 4, illustrating the relative positions of separated blood components during an exemplary blood component collection procedure.

One example of the chamber 66 itself is illustrated in greater detail in FIGS. 4-6. In the illustrated embodiment, the processing chamber 66 is preformed in a desired shape and configuration, e.g., by injection molding, from a rigid, biocompatible plastic material, such as a non-plasticized medical grade acrylonitrile-butadiene-styrene (ABS). All contours, ports, channels, and walls that affect the blood separation process are preformed in a single, injection molded operation. Alternatively, the chamber 66 can be formed by separate molded parts, either by nesting cup shaped subassemblies or two symmetric halves.

The underside of the chamber 66 includes a shaped receptacle which is suitable for receiving an end of the umbilicus 92. A suitable receptacle and the manner in which the umbilicus cooperates with the receptacle to deliver fluid to and remove fluid from the chamber 66 are described in greater detail in U.S. Patent Application Publication No. 2009/0215602.

The illustrated chamber 66 has radially spaced apart inner (low-g) and outer (high-g) side wall portions 94 and 96, respectively, a bottom or first end wall portion 98, and a cover or second end wall portion (not illustrated). The cover comprises a simple flat part that can be easily welded to the remainder of the chamber 66. Because all features that affect the separation process are incorporated into one injection molded component, any tolerance differences between the lid and the remainder of the chamber 66 will not affect the separation efficiencies of the chamber 66. The wall portions 94 and 96, the bottom 98, and the cover together define an enclosed, generally annular channel 100.

The (whole blood) inlet 82 communicating with the channel 100 is defined between opposing interior radial walls 102 and 104. One of the interior walls 102 joins the outer (high-g) wall portion and separates the upstream and downstream ends of the channel 100. The interior walls 102 and 104 define the inlet passageway 82 of the chamber 66 which, in one flow configuration, allows fluid to flow from the umbilicus to the upstream end of the channel 100 at a location which is adjacent the outer or high-g side wall portion 96.

A dam or barrier 106 is formed at a downstream end of the channel 100 and has upstream and downstream sides 108 and 110 (FIG. 4). The barrier 106 extends from the outer side wall portion 96 radially inward to a location which is spaced from the inner side wall portion 94. The barrier 106 will be described in further detail below.

In the embodiment of FIG. 5, the barrier 106 extends for the entire axial height of the channel 100, except for an underpass 112 located at an intermediate axial position spaced below the top of the channel and above, but adjacent to, the bottom 98 of the chamber 66. The underpass 112 is positioned in the channel 100 and defines an opening or passageway through or below the barrier 106, thereby allowing for communication between the upstream and the downstream sides 108 and 110 of the barrier 106. The underpass 112, and particularly the underpass inlet and outlet openings, are preferably located near or in the proximity of the high-g side wall portion 96, where higher density cell components, such as red cells, may accumulate under centrifugal force. More specifically, the high-g side wall portion 96 has a radially outward indent or recess on either side of the barrier 106. As seen in FIG. 5, sections 114 and 116 of the outer side wall portion 96 just upstream and downstream of the barrier 106 extend radially outward from (i.e., are located at a greater radial distance than) a more upstream section of the outer side wall portion 96. An outer radial surface of the underpass 112 may be formed in part by one or more of these radially outward sections 114 and 116 of the outer side wall portion 96 (which sections 114 and 116 are shown removed in FIG. 5). An opposed inner radial surface of the underpass 112 (visible in FIG. 5 beneath the barrier 106) may be formed at a radial location which is approximate to that of the outer or high-G wall portion 96.

A second flow path, referred to herein as a low-g flow path and generally indicated at 118, also communicates between the upstream and downstream sides 108 and 110 of the barrier 106. As shown in FIG. 4, the low-g flow path 118 is distinguishable from the underpass 112 for a number of reasons. For one, the low-g flow path 118 is defined between the barrier 106 and the inner side wall portion 94, allowing for fluid flow around, rather than through or below the barrier 106. It will be seen that the low-g flow path 118 is positioned at a more radially inward location than the underpass 112, making the low-g flow path 118 suitable for accommodating flow of a less dense fluid component, such as plasma, that may accumulate along the inner side wall portion 94, as will be described in greater detail herein. Further, the illustrated low-g flow path 118 is positioned adjacent to the top of the channel 100, with a bottom or lower axial surface of the low-g flow path 118 being defined by an intermediate end wall portion 120, in contrast to the underpass 112, which is positioned adjacent to the bottom 98 of the chamber 66 (FIG. 5).

As shown in FIG. 4, the low-g flow path 118 may include both non-radial and radial portions or legs 122 and 124, respectively, giving the low-g flow path 118 a generally L-shaped configuration. In the illustrated embodiment, the non-radial or annular portion or leg 122 is defined by the space between the inner side wall portion 94 and a radially inward surface of the barrier 106. The illustrated radial portion or leg 124 is defined by the downstream side 110 of the barrier 106 and an interior radial wall extension 126. The interior radial wall extension 126 of FIGS. 4 and 5 terminates at an outer edge 128 which is located at an intermediate radial location between the inner and outer side wall portions 94 and 96.

The illustrated chamber 66 further includes first and second outlets 84 and 86, respectively, which may be defined by opposing surfaces of interior radial walls. The first (plasma) outlet 84 communicates with the channel 100 upstream of the barrier 106. The second (red blood cell) outlet 86 communicates with the channel 100 downstream of the barrier 106. Both the first and second outlets 84 and 86 extend radially inward from the channel 100. The first outlet 84 extends radially inward from an opening 130 which, in the illustrated embodiment, is located at the inner side wall portion 94. The second outlet 86 extends radially inward from an opening 132 that communicates with the downstream side of the barrier 106. In one embodiment, the opening 130 of the first outlet 84 is disposed at approximately a 45 degree angle relative to the opening 132 of the second outlet 86, although other angles and orientations are also possible.

III. The Centrifuge Station

As for the centrifuge station 44 which functions to receive and rotate the chamber 66, it is of the type which supports the chamber 66 while components of the centrifuge station 44 spin around a central axis under the power of an electric drive motor or rotor. The centrifuge station 44 includes a yoke member for engaging the umbilicus 92 extending between the chamber 66 and the cassette 28 in an upside-down question-mark shape. The yoke member causes the umbilicus 92 to orbit around the chamber 66 at a one omega rotational speed. The umbilicus 92 twists about its own axis as it orbits around the chamber 66. The twisting of the umbilicus 92 about its axis as it rotates at one omega with the yoke member imparts a two omega rotation to the chamber 66, according to known design. The relative rotation of the yoke member at a one omega rotational speed and the chamber 66 at a two omega rotational speed keeps the umbilicus 92 untwisted, avoiding the need for rotating seals. A suitable centrifuge station 44 for use with the illustrated chamber 66 is described in greater detail in U.S. Patent Application Publication No. 2009/0215602.

Blood is introduced into and separated within the processing chamber 66 as it rotates. As the processing chamber 66 rotates, the umbilicus 92 conveys whole blood into the channel 100 through the passage 82, where it separates as a result of centrifugal forces.

FIG. 6 shows the relative positions of a radially innermost layer 134, a radially outermost layer 136, and a radially intermediate or interface layer 138 of separated blood components during a typical procedure when the chamber 66 is used to fractionate an amount of blood. The radially innermost layer 134 is positioned adjacent to the inner (low-g) wall portion 94 and, in one embodiment, will be substantially comprised of plasma. The radially outermost layer 136 is positioned adjacent to the outer (high-g) wall portion 96 and, in one embodiment, will be substantially comprised of red blood cells. The interface layer 138 is located radially intermediate the other layers 134 and 136 and, in one embodiment, will be substantially comprised of white blood cells and platelets.

The constitution of the various layers illustrated in FIG. 6 may vary according to the particular procedure. For example, when the chamber 66 is spun at a relatively high speed the radially innermost layer 134 will comprise substantially cell-free plasma, whereas the innermost layer 134 will instead comprise a mixture of plasma and platelets (referred to herein as a "plasma/platelet layer") when a slower spin speed is employed. In other procedures, the radially innermost layer 134 may also contain an amount of anticoagulant, white blood cells, and/or a non-plasma platelet storage solution.

Regardless of the exact composition of the various layers, the radially outermost layer 136 will flow through the underpass 112 (FIG. 5) to the downstream side 110 of the barrier 106 and into the opening 132 of the second outlet 86, where it exits the channel 100 (FIG. 6). A portion of the radially innermost layer 134 will enter the opening 130 of the first outlet 84 and exit the channel 100 therethrough, upstream (approximately 40-45°) of the barrier 106. Another portion of the radially innermost layer 134 will flow past the opening 130 and into the low-g flow path 118, but is prevented from flowing into the opening 132 of the second outlet 86 by the presence of the denser outermost layer 136 on the downstream side 110 of the barrier 106. As for the interface layer 138, it will engage against the upstream side of the barrier 106 and accumulate without exiting the channel 100. A method of collecting the blood components in the interface layer 138 will be described in greater detail herein.

IV. Other Components of the Durable System

In addition to the centrifuge station 44 and pump and valve station 30, the case 18 may include other components compactly arranged to aid blood processing. For example, the case 18 may include a weigh station 140, an operator interface station 142, and one or more trays 144 or hangers 146 for containers. The arrangement of these components in the case 18 can vary. In the illustrated embodiment, the weigh station 140, the hangers 146, the controller 16, and the user interface station 142, like the pump and valve station 30, are located in the lid 22 of the case 18. The holding trays 144 are located in the base 20 of the case 18, adjacent the centrifuge station 44.

The illustrated weigh station 140 comprises a series of container hangers 146 arranged along the top of the lid 22 from which selected containers of the flow set 12 are suspended. The containers receive blood components separated during processing. The weigh station 140 includes weight sensors (which may be incorporated into the structure of the hangers 146) which provide output reflecting weight changes over time. This output is conveyed to the controller 16, which processes the incremental weight changes to derive fluid processing volumes and flow rates. The controller generates signals to control processing events based, in part, upon the derived processing volumes.

The holding trays 144 comprise molded recesses in the base 20 which accommodate selected containers of the flow set 12. and may also include weight sensors.

Using the weight sensors, the controller 16 can continuously determine the actual volume of fluid that is moved per pump stroke and correct for any deviations from commanded flow. The controller 16 can also diagnose exceptional situations, such as leaks and obstructions in the fluid path. This measure of monitoring and control is desirable in an automated apheresis application, where it is desirable for anticoagulant to be accurately metered with the whole blood as it is drawn from the donor, and where product quality (e.g., hematocrit, plasma purity) may be influenced by the accuracy of the pump flow rates.

Alternatively, rather than employing weight sensors, flow monitoring can be achieved by electrical monitoring means, such as a metal electrode located in the chamber of each pump station of the cassette. Suitable flow and weight monitoring arrangements are described in greater detail in U.S. Patent Application Publication No. 2009/0215602.

V. The Controller

The controller 16 carries out process control and monitoring functions for the system. In one embodiment, the controller 16 comprises a main processing unit (MPU), which can comprise, e.g., a Pentium™ type microprocessor made by Intel Corporation, although other types of conventional microprocessors can be used. The controller 16 may be mounted inside the lid 22 of the case 18, adjacent to the operator interface system 142. The controller 16 is programmed to execute at least one blood processing application but, more advantageously, is programmed to execute a variety of different blood processing applications. For example, the controller 16 may be programmed to carry out one or more of the following: a double unit red blood cell collection procedure, a plasma collection procedure, a plasma/red blood cell collection procedure, and a red blood cell/platelet/plasma collection procedure. The details of an exemplary red blood cell/platelet/plasma procedure will be described later. Additional or alternative procedure applications can be included without departing from the scope of the present disclosure. A more detailed description of the programming and functionality of a suitable controller can be found in U.S. Patent Application Publication No. 2009/0215602.

The operator interface station 142 is associated with the MPU to allow the operator to view and comprehend information regarding the operation of the system. The interface station 142 also allows the operator to select applications to be executed by the controller 16, as well as to change certain functions and performance criteria of the system. In the illustrated embodiment, the interface station 142 includes touch screen carried in the lid 22. The interface screen displays information for viewing by the operator in alpha-numeric format and as graphical images. It receives input from the operator by conventional touch activation. In other embodiments, the screen may omit touch-activation capabilities and instead include an associated keypad for entering commands and data.

VI. Exemplary Processing Procedure

An exemplary blood separation procedure will now be described. The following procedure is used to separate donor blood into its components and collect amounts of red blood cells, platelets, and platelet poor plasma for later use.

A. Pre-Processing

Prior to processing, an operator selects the "RBC/Platelet/Plasma" protocol using the operator interface station 142. If the blood source is a donor, the operator then proceeds to enter various parameters, such as the donor gender/height/weight. In one embodiment, the operator also enters the target yield for the various blood components. In an exemplary procedure, the pre-selected yields are one unit each of single dose platelets, packed red cells, and platelet poor plasma. As will be described in greater detail herein, an amount of plasma may be used to harvest platelets and packed red cells from the chamber and act as a platelet storage fluid, so it may be advantageous to specify an additional amount of plasma (e.g., approximately 335 ml extra—300 ml to harvest and store the platelets and 35 ml to harvest the packed red cells) to ensure that one unit remains in the plasma collection container after the platelets and packed red cells have been harvested.

The operator also selects the collection control system, which may be based on, for example: (1) the amount of whole blood to process, (2) a donor platelet pre-count (i.e., the amount of platelets in a pre-donation sample of the donor's blood) and the target platelet yield, or (3) the target platelet yield alone (when no platelet pre-count is available).

Further, before processing begins, any separate containers (e.g., a platelet storage solution container) are connected to the flow set 12 and the flow set 12 is secured to the blood processing device 14. An integrity check of the flow set 12 may be executed by the controller 16 to ensure the various components are properly connected and functioning. Following a successful integrity check, the blood source is connected to the flow set 12 (e.g., by phlebotomizing a donor), and the chamber 66 is primed by saline pumped from the saline container 52 by operation of one or more pumps of the cassette 28.

B. Blood Draw

Figure 7A:
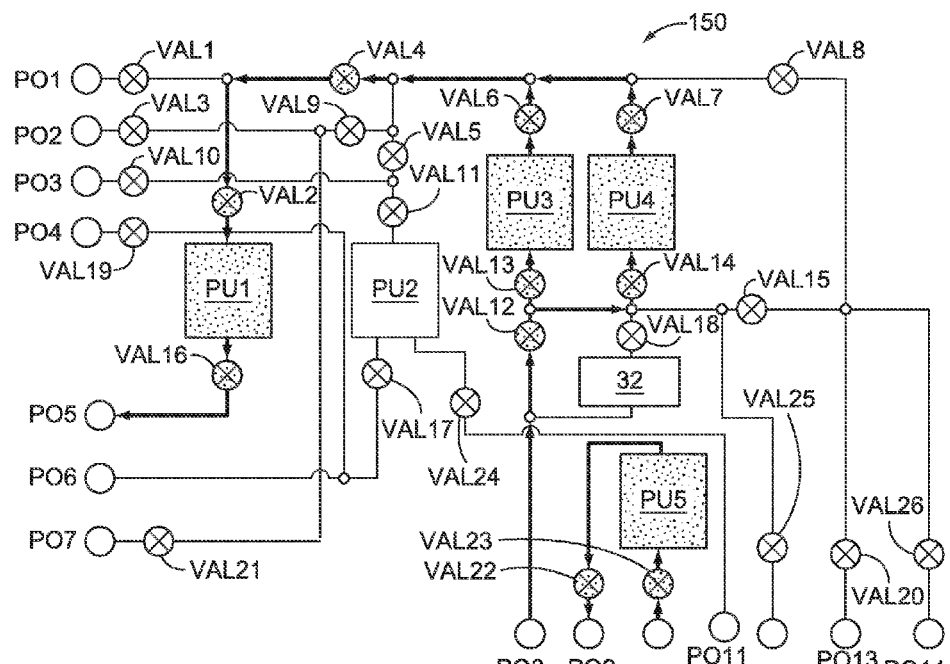
FIGS. 7A and 7B are schematic views of the blood processing circuit of FIG. 3, showing the programming of the cassette to carry out different fluid flow tasks in connection with drawing whole blood from a blood source.
Figure 7B:
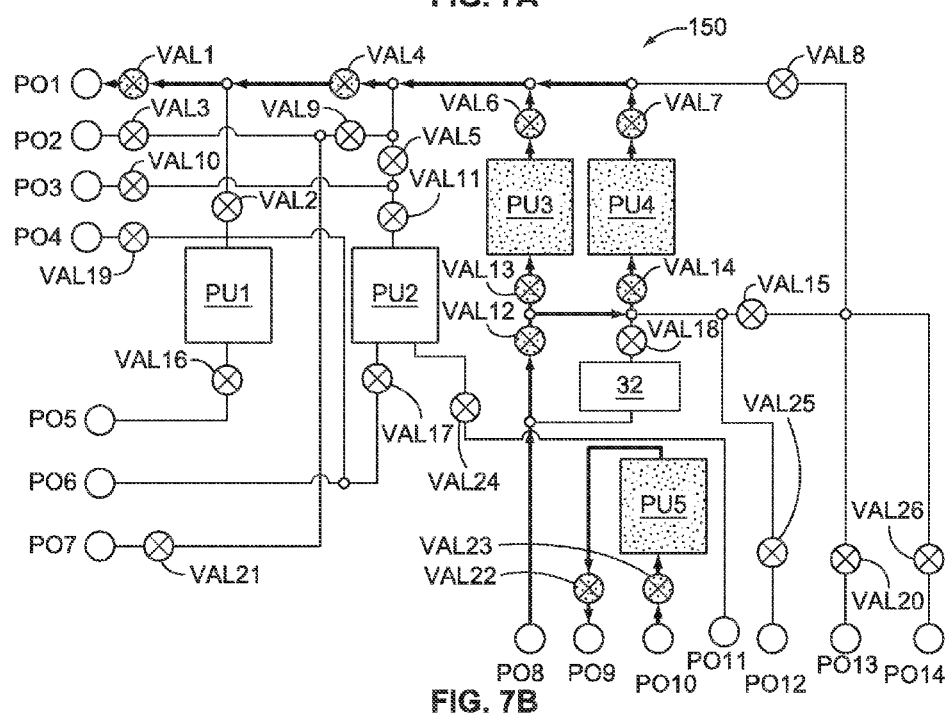

Once the pre-processing tasks have been performed by the system and the operator, a blood draw stage begins. Blood is continuously drawn from the blood source and into the flow set 12 at a draw flow rate by a two-phase process that is illustrated in FIGS. 7A and 7B. Before the blood enters the cassette 28 in either of the phases, an amount of anticoagulant is added to it. Anticoagulant is continuously pumped from the anticoagulant container 48 (which is connected via tubing to port PO10 of the cassette 28) at an anticoagulant flow rate, through the cassette flow circuit (identified in FIG. 3 as element 150), and out port PO9 of the cassette 28 by operation of the anticoagulant pump PU5. The anticoagulant travels through the tubing 88 connected to the port PO9 and exits through the y-connector 90, where it mixes with blood flowing from the blood source into the cassette 28 via port PO8.

FIG. 7A schematically illustrates the path through the cassette 28 taken by anticoagulated whole blood being pumped from the blood source (which is connected via tubing to port PO8 of the cassette 28), through the cassette flow circuit 150, and directly into the chamber 66 (which is connected via tubing to port PO5 of the cassette 28). The donor pumps PU3/PU4 cooperate with the in-process pump PU1 to flow the blood through the cassette flow circuit 150 in this first phase.

In the phase illustrated in FIG. 7B, anticoagulated blood is pumped from the blood source, through the cassette flow circuit from port PO8 to port PO1, and to the in-process container 80 instead of flowing directly into the chamber 66 via port PO5. In contrast to the first phase, the operation of just the donor pumps PU3/PU4 is sufficient for flowing the blood into the in-process container 80 in the phase of FIG. 7B. The blood pumped into the in-process container 80 is temporarily stored therein before it is eventually pumped into the chamber 66, as will be described in greater detail herein.

In one embodiment, blood is drawn from the source by one of the donor pumps PU3/PU4 while the other donor pump PU3/PU4 expels the blood to the chamber 66 or the in-process container 80. This allows for simultaneous blood draw and pumping to the chamber 66 or the in-process container 80.

The blood may be alternately pumped to the chamber 66 (FIG. 7A) and then to the in-process container 80 (FIG. 7B) at a particular ratio (e.g., 9:1) to fill both at the same time.

C. Blood Separation

The blood in the chamber 66 is subjected to a separation stage, wherein separation of the fluid components occurs based on density, as shown in FIG. 6, while the chamber spins at a "hard spin" rate of, for example, approximately 4500 RPM. It is noted that the angular velocities used herein conventionally are "two omega" (i.e., the spin speed of the chamber itself) although "one omega" (i.e., the speed at which the umbilicus is orbited around the chamber) may also be used, as well as some combination thereof. A higher density component such as red blood cells is forced towards the outer or high-side wall portion in an outermost layer 136 and a lower density component such as platelet poor plasma is forced towards an inner or low-g side wall portion in an innermost layer 134. The interface layer 138 between the red blood cells and the plasma contains a buffy coat layer which includes at least a portion of platelets and white blood cells, although the components of the interface will vary based on the particular procedure employed.

D. Blood Component Collection

1. Initial Plasma and Red Cell Collection

Figure 8:
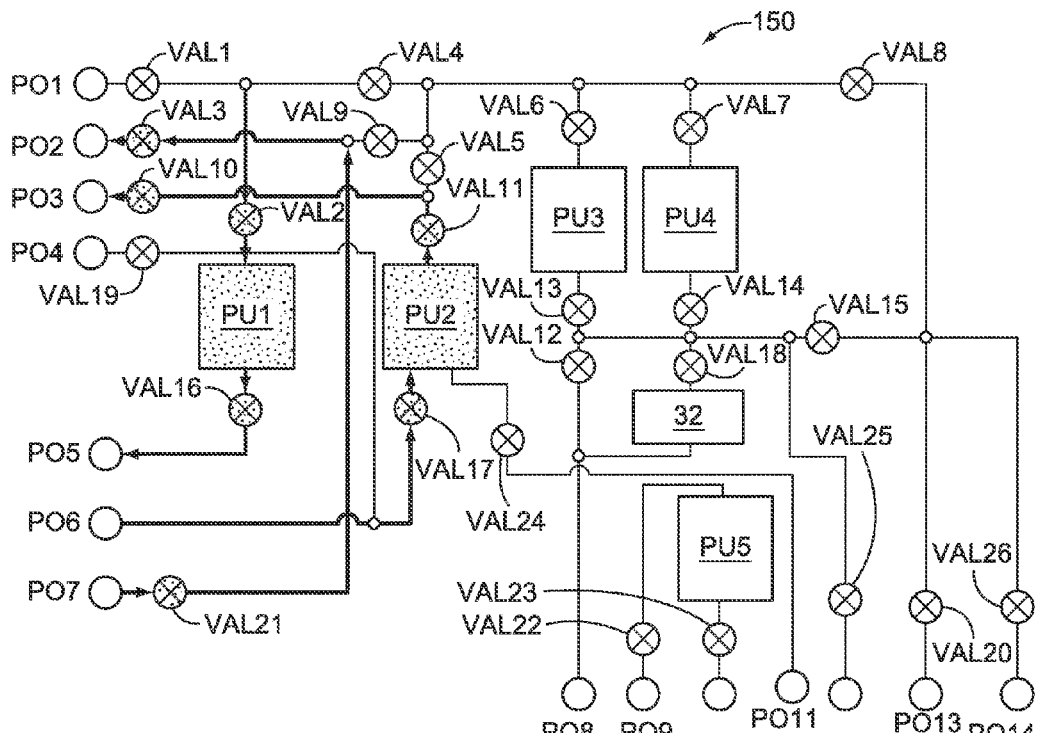
FIG. 8 is a schematic view of the blood processing circuit of FIG. 3, showing the programming of the cassette to carry out different fluid flow tasks in connection with separating whole blood into constituent layers.

As the interface is pooling upstream of the barrier 106, fluid may be collected separately from either side of the interface—or both sides thereof—through the respective outlet 84 or 86 depending on the requirements of the procedure. For example, FIG. 8 schematically illustrates the path of whole blood out of port PO5 of the cassette 28 and into the chamber 66, with the blood separating into its constituent parts and some platelet poor plasma exiting the chamber 66 through the plasma outlet 84 (per FIG. 6). The plasma exiting the plasma outlet 84 flows through tubing and into the cassette 28 via port PO6 of the cassette 28. When the plasma enters the cassette fluid circuit 150, the plasma pump PU2 cooperates with the various valves to convey the plasma to port PO3 of the cassette 28. The plasma exiting port PO3 travels through tubing and into the plasma collection container 62.

Simultaneously, some red blood cells are collected radially outward of the interface, exiting the chamber 66 through the red blood cell outlet 86 (per FIG. 6). The red blood cells exiting the red blood cell outlet 86 flow through tubing and into the cassette 28 via port PO7 of the cassette 28. When the red blood cells enter the cassette fluid circuit 150, they are directed to port PO2 of the cassette 28. The red blood cells exiting the port PO2 travel through tubing and into the red blood cell collection container 64.

2. Platelet Accumulation

While the plasma and red blood cells are being separated and removed from the chamber 66, the barrier 106 allows for accumulation of platelets (which are contained in the buffy coat/interface layer 138) in the channel 100, substantially without the platelets exiting the chamber 66 (per FIG. 6).

In one embodiment, the stages of drawing whole blood into the chamber and collecting platelet poor plasma and red blood cells (while retaining buffy coat in a pool upstream of the barrier 106) are repeated until a predetermined amount of platelets is present in the pooled buffy coat. In one embodiment, the low-g and high-g walls are sufficiently spaced from each other to allow for at least one therapeutic unit of single dose platelets, or approximately $3.0\text{-}4.7\times10^{11}$, platelets to be pooled upstream of the barrier without allowing the pooled buffy coat to spill past the barrier 106. In another embodiment, the low-g and high-g walls are sufficiently spaced from each other to allow for at least approximately $7\times10^{11}$ platelets to be pooled upstream of the barrier without allowing the pooled buffy coat to spill past the barrier 106.

Typically, the amount of blood that must be processed to collect one therapeutic unit of single dose platelets results in a surplus of separated platelet poor plasma and red blood cells. Accordingly, periodically during the platelet pooling process, an amount of the collected platelet poor plasma and red blood cells may be returned to the blood source or otherwise conveyed to a recipient.

At the end of the platelet pooling process and when it has been determined that the required amounts of plasma, red blood cells, and platelets are present in the system, any excess collected red blood cells and plasma may be returned to the donor, followed by the donor being disconnected from the system. An additional amount of red blood cells may be conveyed to the donor, with the understanding that the red blood cell harvesting stage (which will be described in greater detail herein) will ultimately bring the amount of collected red blood cells up to the target yield.

3. Recombination and Recirculation

Figure 9A:
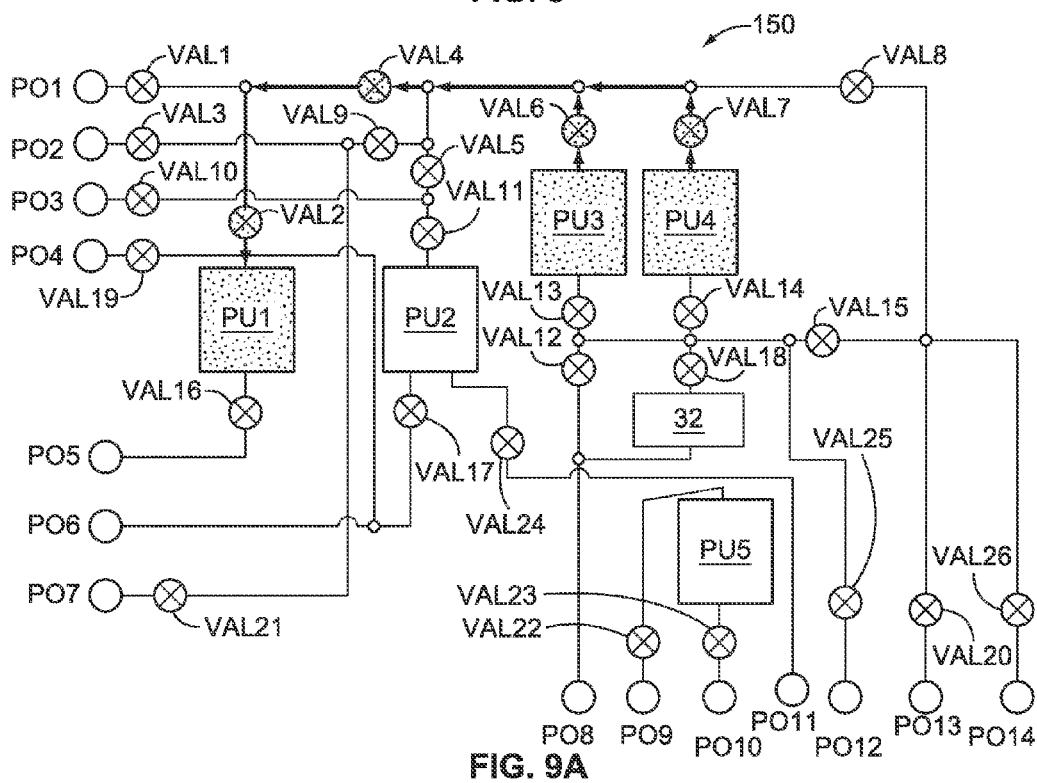
FIGS. 9A and 9B are schematic views of the blood processing circuit of FIG. 3, showing the programming of the cassette to carry out different fluid flow tasks in connection with recombining the previously separated blood components.
Figure 9B:
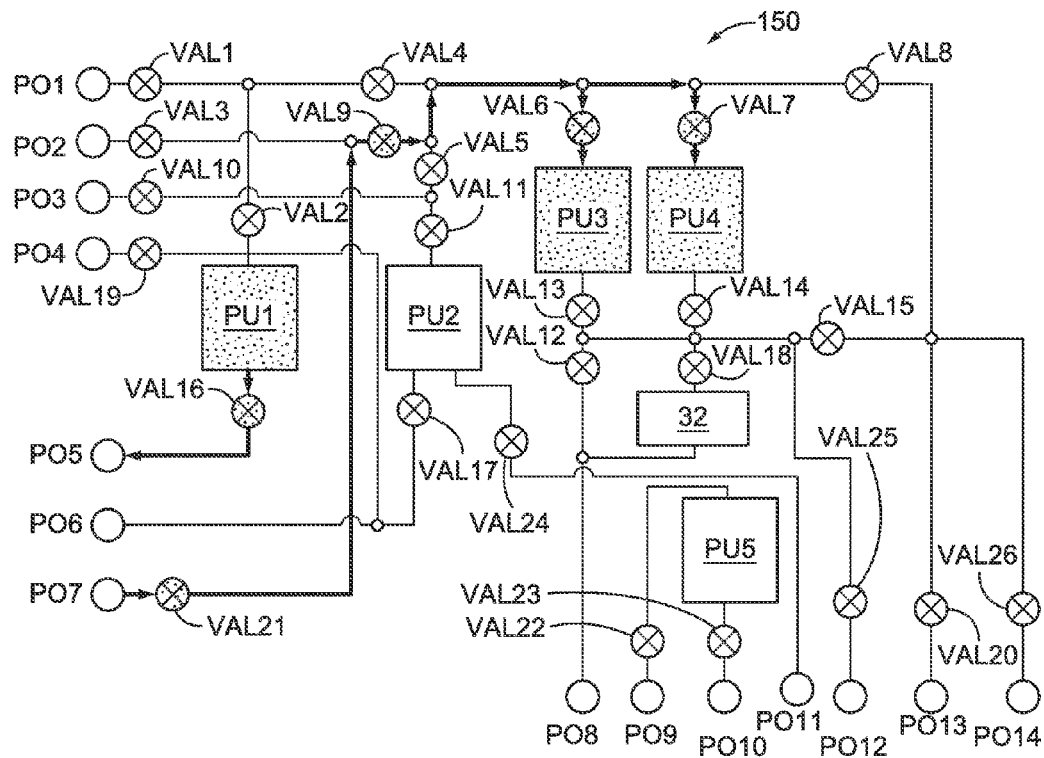

Next, the separated fluid components within the chamber 66 are recombined. FIGS. 9A and 9B illustrate the operation of the cassette 28 during the recombination stage. In one embodiment, recombination is performed by rotation of the chamber 66 in both clockwise and counterclockwise directions, whereby the chamber 66 is rotated alternately in clockwise and counterclockwise directions one or more times. During this recombination stage, the valves VAL17 and VAL19 associated with the plasma outlet 84 (which is connected via tubing to port PO6 of the cassette 28) are closed. With the plasma outlet 84 effectively closed, the contents of the chamber 66 are forced to exit or enter the chamber 66 via the whole blood inlet 82 and/or the red blood cell outlet 86. The donor pumps PU3 and PU4 and the in-process pump PU1 of the cassette 28 are operated to cycle the blood components into and out of the chamber 66, as generally illustrated in the two-phase process of FIGS. 9A and 9B.

In the phase illustrated in FIG. 9A, the blood components present in the donor pumps PU3 and PU4 are pumped through the cassette flow circuit 150 to the in-process pump PU1. In the phase illustrated in FIG. 9B, the blood components present in the in-process pump PU1 are pumped through the chamber 66 (in through the whole blood inlet 82 via cassette port PO5 and out the red blood cell outlet 86 via cassette port PO7) and into the donor pumps PU3 and PU4. These phases alternate as the chamber 66 is rotated alternately in clockwise and counterclockwise directions.

The recombination stage results in a uniform blood-like mixture which includes plasma, red blood cells, platelets, and white blood cells having an approximate hematocrit of 20-40 percent (in one embodiment). The recombination stage may last approximately one to three minutes, although this time period may vary. The rotation of the chamber in either direction may be at a rate much lower than the rate of rotation during initial separation of the components and may be, for example, in the range of approximately 300 to 600 RPM, although other rates of rotation are possible.

After a sufficient recombination period, the first phase of a recirculation stage begins by causing the chamber 66 to rotate in a uniform (i.e., non-alternating) direction. The flow of fluid within the chamber 66 is generally directed from the inlet 82 to the first and second outlets 84 and 86, although fluid is still prevented from exiting the chamber via the plasma outlet 84. The specific speed of the rotor of the centrifuge station 44 may vary, but may be a "slow spin" of approximately 2500-2700 RPM, which separates a red blood cell layer from a layer containing plasma and platelets. During this time, the valves VAL17 and VAL19 associated with cassette port PO6 are closed, effectively closing the plasma outlet 84 and forcing the fluid in the chamber 66 to exit via the red blood cell outlet 86 (which is connected via tubing to port PO7 of the cassette 28) and flow into the donor pumps PU3 and PU4, identical to the second phase of the recombination stage shown in FIG. 9B. The donor pumps PU3 and PU4 pump the fluid through the cassette flow circuit 150 to the in-process pump PU1 (identical to the first phase of the recombination stage shown in FIG. 9A). Finally, the in-process pump PU1 pumps the fluid out of port PO5, through the whole blood inlet 82, and back into the channel 100. This phase of the recirculation stage continues for a sufficient time to allow the red blood cell layer to settle within the chamber 66.

Figure 10A:
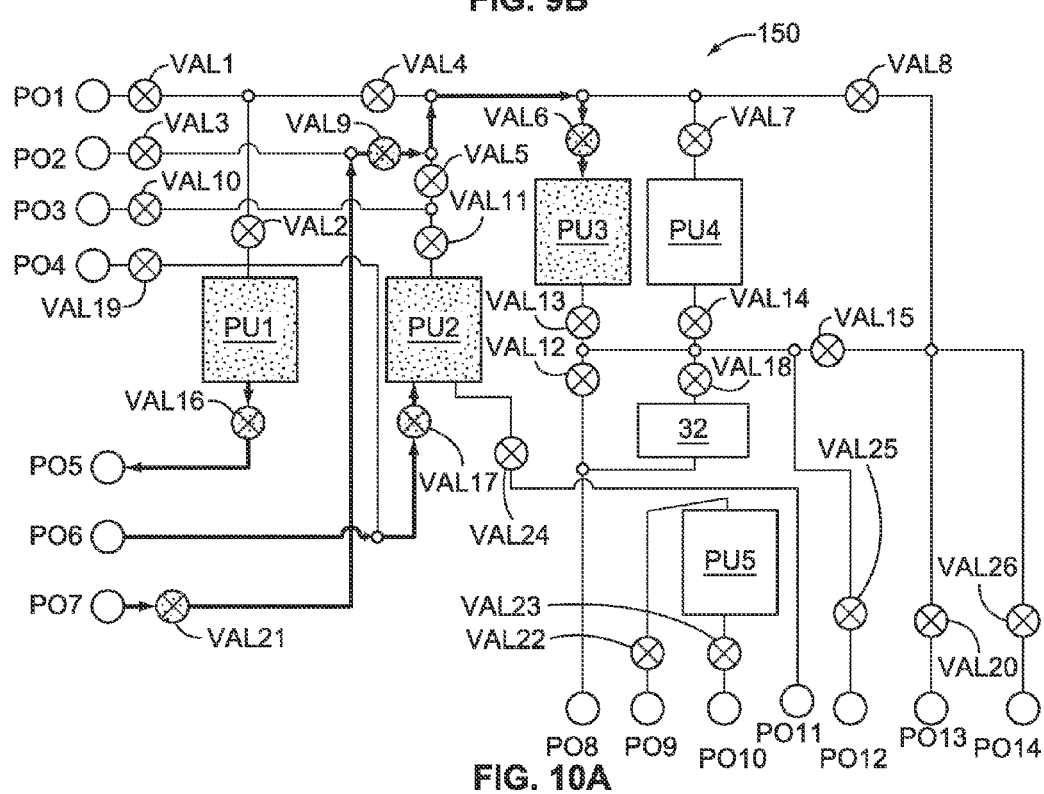
FIGS. 10A and 10B are schematic views of the blood processing circuit of FIG. 3, showing the programming of the cassette to carry out different fluid flow tasks in connection with re-separating the previously recombined blood components.

After the red blood cell layer has settled within the chamber 66, the second phase of the recirculation stage may begin. Valve VAL 17 is opened, as shown in FIG. 10A, allowing flow through cassette port PO6 and effectively re-opening plasma outlet 84 (which is connected via tubing to port PO6). During this phase, the red blood cell layer continues exiting the chamber 66 via the red blood cell outlet 86, flowing into the cassette flow circuit 150 via port PO7, and being directed to one of the donor pumps P03. With the plasma outlet 84 re-opened, the layer including plasma and platelets is allowed to exit the chamber therethrough and enter the cassette flow circuit 150 via port PO6. The plasma/platelet layer is directed from port PO6 to the plasma pump PU2, as shown in FIG. 10A.

Thereafter, the contents of the donor pump PU3 (i.e., the red blood cell layer) and the plasma pump PU2 (i.e., the plasma/platelet layer) are pumped through the cassette flow circuit 150 and into the in-process pump PU1 (FIG. 16B), where they are recombined. The in-process pump PU1 subsequently pumps the combined fluids out of the cassette 28 via port PO 5 and back to the chamber 66 (FIG. 16A). These sub-phases alternate, thereby creating a recirculation loop into and out of the chamber 66.

During recirculation, no plasma, platelets, or red blood cells are collected. The platelet concentration in the plasma/platelet layer generally increases during this phase, with platelets from the interface becoming suspended in the plasma.

Recirculation of the plasma/platelet layer may continue for several minutes (approximately two to four minutes in one embodiment), which duration may vary depending upon the particular procedure. The recirculation stage ends when an optical sensor associated with the tubing 152 connecting the plasma outlet 84 and cassette port PO6 detects a plasma/platelet layer which has a desired concentration of platelets and which is visually low in red blood cells (e.g., a hematocrit between approximately 20-40 percent, as noted above). A suitable optical sensing system is described in greater detail in U.S. Patent Application Publication No. 2009/0215602.

4. Platelet Collection

After the recirculation stage and any additional blood processing stages (if it is determined during the recirculation stage that additional blood collection and processing are required to collect the target amount of platelets), a platelet harvesting stage is initiated. In the platelet harvesting stage, the plasma/platelet layer is pumped out of the chamber 66 via the plasma outlet 84 and into the platelet collection container 60. This is achieved by continuing the immediately preceding recirculation stage, but adding a platelet storage fluid (platelet poor plasma from the plasma collection container 62 and/or non-plasma storage solution from the platelet storage solution container) to the circulating fluid. The additional fluid replaces the fluid volume lost within the chamber 66 due to collection of the plasma/platelet layer.

Figure 10B:
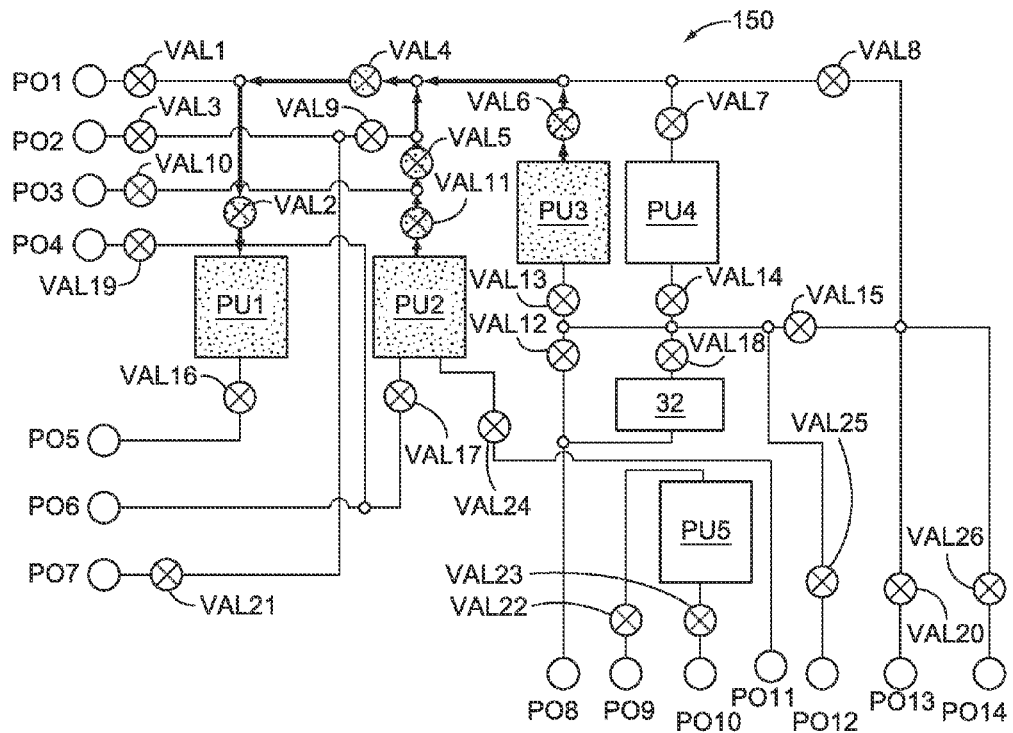

In particular, as shown in FIG. 10B, the contents of the plasma pump PU2 (i.e., the plasma/platelet layer) and the contents of the donor pump PU3 (i.e., the red blood cell layer) flow to the in-process pump PU1. The mixed contents of the in-process pump PU1 are then pumped out of cassette port PO5 and into the chamber 66, as packed red cells exit the chamber 66 via the red blood cell outlet 86 and are pumped through cassette port PO7 into the donor pump PU3 (FIGS. 17A/17B). Simultaneously, the plasma/platelet layer exits the chamber 66 via the plasma outlet 84 and is pumped through cassette port PO6, through the cassette flow circuit 150, and out port PO4 to the platelet collection container 60 (FIGS. 17A/17B). Rather than being filled with the plasma/platelet layer (as in the recirculation stage), the plasma pump PU2 is filled with a platelet storage fluid. In one embodiment, illustrated in FIG. 11A, the plasma pump PU2 is filled with plasma from the plasma collection container 62 (which is connected via tubing to port P03 of the cassette 28). In another embodiment, illustrated in FIG. 11B, the plasma pump PU2 is instead filled with non-plasma storage solution from the platelet storage solution container (which is connected via tubing to port PO11 of the cassette 28).

With this additional fluid in the plasma pump PU2, the contents thereof and the contents of the donor pump PU3 again flow into the in-process pump PU1 (FIG. 16B). Finally, the in-process pump PU1 is emptied into the chamber 66 through the whole blood inlet 82 (which is connected via tubing to port PO5 of the cassette 28), with the plasma/ platelet layer being displaced out of the plasma outlet 84 and into the cassette flow circuit 150 via port PO6 (alternatively illustrated in FIGS. 11A and 11B). Once in the cassette 28, the plasma/platelet layer is pumped from port PO6 to port PO4 and to the platelet collection container 60. Simultaneously, the packed red cells flow from the red blood cell outlet 86 of the chamber 66, into the cassette flow circuit 150 via port PO7, and through the cassette flow circuit 150 to the donor pump PU3 (alternatively illustrated in FIGS. 11A and 11B). These sub-phases alternate (i.e., between the sub-phase illustrated in FIG. 10B and the sub-phase illustrated in FIGS. 11A/11B), thereby creating a recirculation loop into and out of the chamber 66, with an amount of the plasma/platelet layer being collected during each iteration of the loop.

Figure 11A:
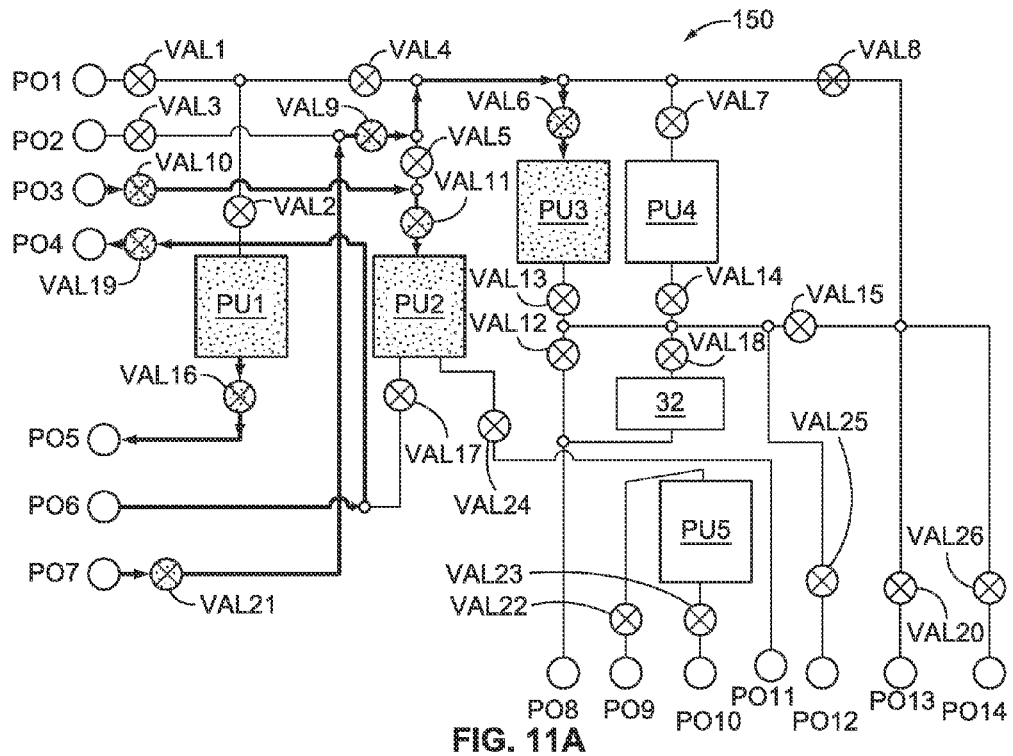
FIG. 11A is a schematic view of the blood processing circuit of FIG. 3, showing the programming of the cassette to carry out different fluid flow tasks in connection with harvesting platelets using platelet poor plasma.
Figure 11B:
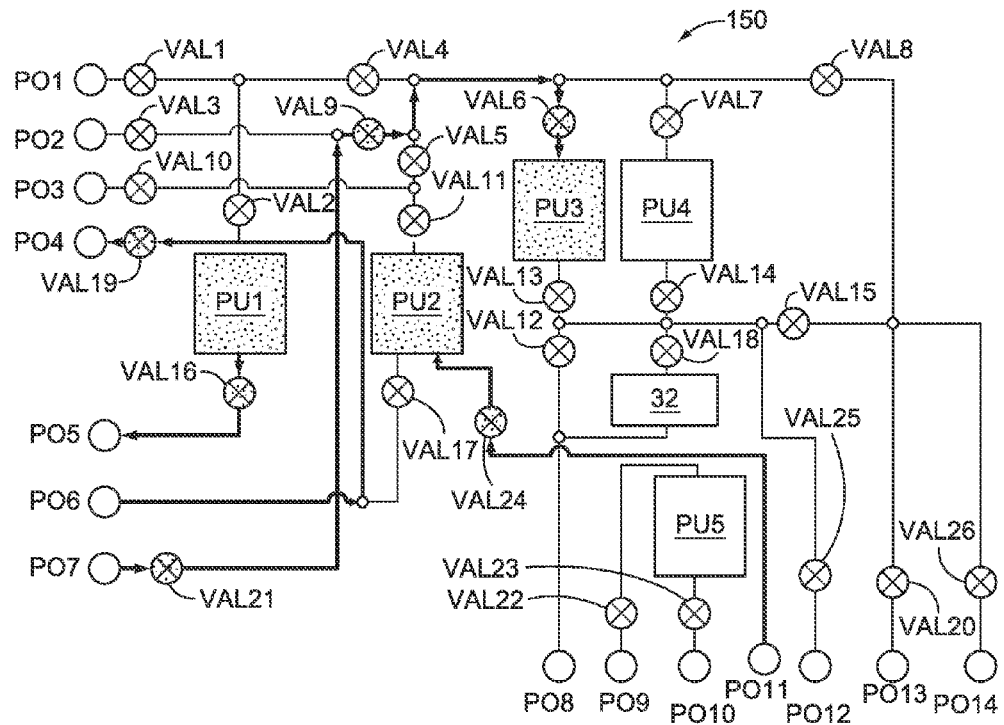
FIG. 11B is a schematic view of the blood processing circuit of FIG. 3, showing the programming of the cassette to carry out different fluid flow tasks in connection with harvesting platelets using a (non-plasma) platelet storage solution.

The sub-phases illustrated in FIGS. 11A and 11B may be practiced independently (e.g., employing only the sub-phase of FIG. 11A in combination with the sub-phase of FIG. 10B to harvest and store platelets in platelet poor plasma) or combined during a given procedure. For example, the platelet harvesting stage may following a repeating loop from the sub-phase illustrated in FIG. 10B, to the sub-phase illustrated in FIG. 11A, to the sub-phase illustrated in FIG. 10B, to the sub-phase illustrated in FIG. 11B, and finally back to the beginning of the loop. In yet another embodiment, non-plasma storage solution is used to displace and store platelets (i.e., the FIGS. 10B and 10B sub-phases are alternated) until a target amount of storage solution has been used, at which time platelet poor plasma is used to displace and store the platelets (i.e., the FIGS. 10B and 11A sub-phases are alternated) until the target platelet yield is achieved.

When the target platelet yield has been reached, the system may operate to flow plasma and/or non-plasma storage solution directly to the platelet collection container (bypassing the chamber 66) if need be.

Although the majority of leukocytes in the plasma/platelet layer will sediment therefrom during the aforementioned recirculation stages, some leukocytes typically remain in the collected fluid. The illustrated flow set 12 (FIG. 5) has an in-line leukoreduction filter 68 between the cassette 28 and the platelet collection container 60. In such an embodiment, the plasma/platelet layer that is pumped out of the chamber 66 by the plasma pump PU2 is pumped through the leukoreduction filter 68 and into the platelet collection container 60 while the chamber 66 is still spinning and processing the blood components. In one example, a reduction of white blood cells from approximately $1.0 \times 10^7$ to approximately $1.0 \times 10^4$ on account of an in-line leukoreduction filter was observed.

5. Additional Red Cell Collection

Figure 12:
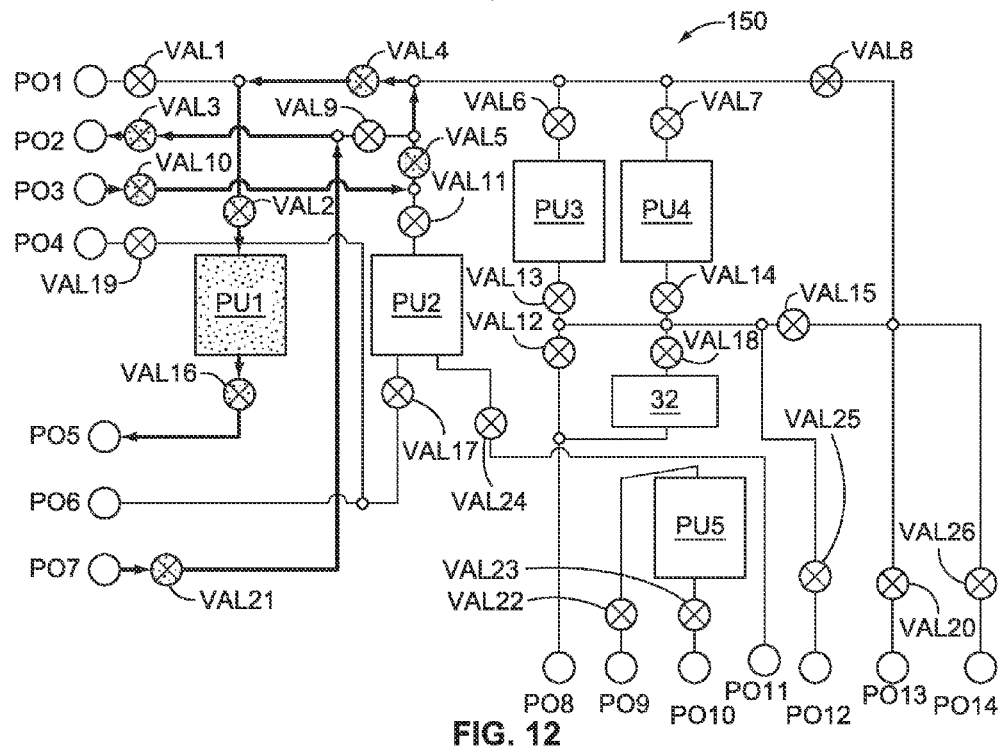
FIG. 12 is a schematic view of the blood processing circuit of FIG. 3, showing the programming of the cassette to carry out different fluid flow tasks in connection with harvesting red blood cells.

When the platelet harvesting stage is complete, the system continues with a red blood cell harvesting stage, which is illustrated schematically in FIG. 12. During this stage, the valves VAL17 and VAL19 associated with cassette port PO6 are closed, effectively closing the plasma outlet 84, and the spin speed of the chamber 66 is increased to a "hard spin" of, for example, approximately 4500 RPM. The in-process pump PU1 delivers platelet poor plasma from the plasma collection container 62 (which is connected via tubing to port P03 of the cassette 28) to the chamber 66 via the whole blood inlet 82 (which is connected via tubing to port PO5 of the cassette 28). The incoming plasma forces the packed red blood cells out of the red blood cell outlet 86 and into the cassette flow circuit 150 via port PO7. The red blood cells are directed through the cassette flow circuit 150, out of port PO2, and to the red blood cell collection container 64. In an alternative embodiment, red blood cells remaining in the chamber 66 may be removed therefrom by other means. For example, rather than employing plasma to flush red blood cells from the chamber 66, another fluid (e.g., saline) or air may be employed.

After the platelets and red blood cells have been collected, any of a number of post-processing procedures may be initiated, a number of which are described in greater detail in U.S. Patent Application Publication No. 2009/0215602.

VII. Limiting Platelet Aggregation

During processing, the platelets in the interface layer 138 within the channel 100 may tend to stick or clump together, particularly when a full dose of platelets (approximately $3.0$-$4.7 \times 10^{11}$ platelets) is held in the channel 100 prior to collection. If the platelets become aggregated, it may be impossible to collect as many of them as desired, as the clumped platelets may not be able to flow readily out of the channel 100 through the appropriate outlet 84. Also, aggregation can result in undesired activation of the platelets, potentially reducing the long term viability. These problems are not unique to the foregoing system and method, but can occur in other platelet collection systems as well.

To avoid or limit such aggregation, the controller may be programmed to monitor the amount of platelets within the blood or in the blood separation device (i.e., the chamber 66 in the illustrated embodiment) and predict the likelihood of platelet aggregation in the device. If the controller determines that the likelihood approaches, meets, or exceeds some predetermined value, the controller may automatically take corrective action to avoid or reduce the risk of platelet aggregation. As used herein, the term "approaches" refers to a situation in which the likelihood, while less than the predetermined value, may be indicative of potential platelet aggregation. More particularly, the term "approaches" may be understood to refer to a situation in which the likelihood is less than the predetermined value, but sufficiently close to give rise to concern, such as being within a particular percentage of the predetermined value. For example, the term "approaches" may be understood to refer to a situation in which the likelihood is less than the predetermined value, but within about 10-15%, and particularly within about 10% of the predetermined value. In yet another embodiment, the term "approaches" may be understood to refer to a situation in which the likelihood is less than the predetermined value, but increasing toward the predetermined value and within a particular percentage (e.g., 10-15%) of the predetermined value. It is within the scope of the present disclosure for such corrective action to encompass steps taken to prevent platelet aggregation from ever occurring and steps taken to counteract platelet aggregation which may have already taken place. However, it is preferred to prevent any platelet aggregation, as it may be difficult to counteract some instances of platelet aggregation once they have already occurred.

In general, the corrective action preferably is in the form of an automatic adjustment to one or more operational parameters of the blood processing protocol. For example, the controller may act to avoid platelet aggregation by changing the ratio of whole blood to anticoagulant in the system. This may be achieved in a number of ways.

One way of varying the ratio of whole blood to anticoagulant in the system is by maintaining the amount of blood in the system or the rate at which blood is drawn into the system, but varying the amount of anticoagulant in the system or the anticoagulant flow rate (i.e., the rate at which anticoagulant is continuously added to the blood in the system). It has been found that the incidence of platelet aggregation decreases with a decreasing whole blood-to-anticoagulant ratio. For example, it has been found that, for a full dose platelet collection protocol according to the foregoing description, by changing the whole blood-to-anticoagulant ratio from 11:1 to 9:1, platelet aggregation may be substantially avoided. Accordingly, in one embodiment, the whole blood-to-anticoagulant ratio is decreased by increasing the amount of anticoagulant added to the blood.

If the pump system is programmed to normally operate at a default anticoagulant flow rate, the controller may adjust the operation of the pump system to operate at an elevated anticoagulant flow rate. The anticoagulant flow rate may be increased from the default rate to the elevated rate over the course of the procedure or immediately. The elevated flow rate may be maintained until the end of the procedure, until some later time in the procedure (at which time the rate decreases to the default rate or changes to some other rate, which may be lower or higher than the elevated flow rate), or may be immediately ended. If the rate at which anticoagulant is added to the system is immediately increased and then immediately returned to the default rate, such corrective action may be characterized as the injection of a large, one-time bolus of anticoagulant. It is also within the scope of the present disclosure for injection of more than one bolus of anticoagulant. The increased amount of anticoagulant may be added to the blood being drawn from the blood source or, particularly in the case of the bolus method, it may be added directly into the separation device.

Alternatively, rather than varying the anticoagulant flow rate or the amount of anticoagulant in the system, the controller may respond to the risk of platelet aggregation by varying the amount of blood drawn into the system or the blood draw rate (i.e., the rate at which blood is continuously drawn from the blood source into the system). As noted above, decreasing the whole-blood-to-anticoagulant ratio tends to decrease the occurrence of platelet clumping, and the controller may achieve this effect by operating the pump system to draw a decreased amount of blood from the blood source (e.g., by actuating the pump system to decrease the blood draw rate). It will be appreciated that such a course of action has a similar effect to adding additional anticoagulant in that it serves to further dilute the blood in the system (i.e., decrease the whole blood-to-anticoagulant ratio), but it may require longer procedure time.

In yet another embodiment, the amount of anticoagulant added to the system (or the anticoagulant flow rate) may be increased in combination with a decrease in the amount of blood drawn into the system (or the blood draw rate). Other methods of modifying the ratio (e.g., by decreasing the anticoagulant flow rate while decreasing the blood draw rate to a larger degree or increasing the blood draw rate while increasing the anticoagulant flow rate to a larger degree) may also be employed without departing from the scope of the present disclosure. Further, the range of possible responses is not limited to actions taken during a blood separation procedure, but may also include actions taken afterward, such as adding an amount of anticoagulant to the chamber after the procedure is completed.

Additionally, the response carried out by the controller need not be a single event, but may comprise a number of predictions and responses. For example, the controller may be programmed with multiple values against which the predicted likelihood of platelet aggregation may be checked. Upon the prediction approaching, meeting, or exceeding a first threshold value, the controller may command the pump system to carry out a first corrective action to avoid platelet clumping. After the first corrective action, the controller again predicts the likelihood of a platelet aggregation and compares it to another predetermined threshold value. If the predicted likelihood approaches, meets, or exceeds this second value, a second corrective action (which may be either the same as the first corrective action or a different response) may be initiated by the controller. In another embodiment, the controller may be programmed to automatically take periodic corrective actions, e.g., at each 50 ml interval of blood drawn into the system. This may be combined with any of the foregoing corrective actions to various effect. For example, the controller may be programmed to increase the anticoagulant flow rate at the designated time for each corrective action, resulting in an anticoagulant infusion profile which ramps upwardly over time as a step function. Other comparison protocols and corrective actions may also be paired together without departing from the scope of the present disclosure.

If the controller includes anti-aggregation protocol, it may affect the default processing parameters. For example, if the controller responds to anticipated or actual platelet aggregation by adding an extra amount of anticoagulant, it may be possible for the procedure to start at a lower anticoagulant flow rate than usual (i.e., a higher whole blood-to-anticoagulant ratio) and then later in the procedure, after platelets have been collected into the separation chamber 66, add a bolus of anticoagulant into the separation chamber 66 to reduce the potential platelet aggregation. By using a relatively low default anticoagulant flow rate, the total amount of anticoagulant used during a procedure may be decreased without unduly increasing the risk of platelet aggregation. Reducing the amount of anticoagulant used is beneficial in terms of both cost savings and decreasing the occurrence of negative donor citrate reactions.

There are various ways in which the controller may predict the likelihood of platelet aggregation. In one embodiment, the controller is programmed to calculate the amount of platelets in the blood and/or in the separation device. The calculation may be carried out using any suitable algorithm and factors. For example, the amount of platelets may be calculated by taking into account the amount of blood drawn, the platelet concentration of the blood, and the mean platelet volume. The platelet concentration may be either determined during the blood separation procedure (using an online estimator, for example) or may be known before the procedure begins (e.g., if the blood source is a human donor with a known platelet pre-count). Similarly, the mean platelet volume may be either determined during the blood separation procedure or may be known before the procedure begins. Any platelet information known prior to processing may be provided to the controller at the time the desired protocol and required parameters (e.g., donor weight, amount of platelets to collect, etc.) are entered.

Alternatively, rather than calculating the amount of platelets, one or more optical sensors may be employed to detect the amount of platelets in the blood and/or in the separation device. The use of optical sensors to determine the presence of platelets in blood or in a separated blood component is well known. Generally speaking, the difference between a baseline optical density of a fluid (e.g., the optical density of plasma substantially free of cellular components) and the actual detected optical density (e.g., the optical density of plasma containing platelets) may be indicative of the platelet concentration of the fluid, so a "snapshot" of the platelet content can be estimated by comparing the two values over a period of time and then integrating the area therebetween during that time. The integrated value is equal to (or at least indicative of) the amount of platelets in the blood and/or in the separation device. One particular system for optically monitoring the platelet content of blood or a separated blood component is described in U.S. Patent Application Publication No. 2009/0215602.

Depending on the configuration of the blood separation system and the separation device, the optical sensor(s) may be variously positioned. For example, when the separation device is opaque and/or it is impracticable to directly monitor the interior of the separation device, one or more optical sensors may be associated with the fluid flow tubes connected to the inlet(s) and outlet(s) of the device. Alternatively, for separation devices having at least a portion that is at least partially transparent or translucent, one or more optical sensors may be positioned to directly monitor the contents of the separation device to determine the amount of platelets therein.

The many features of the present subject matter have been demonstrated by describing their use in separating whole blood into component parts for storage and blood component therapy. This is because the present subject matter is well adapted for use in carrying out these blood processing procedures. It should be appreciated, however, that the described features equally lend themselves to use in other blood processing procedures and the present disclosure is not limited to any particular blood processing procedure.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A blood processing method comprising:
conveying blood into a blood separation device;
determining the amount of platelets in the blood and/or in the blood separation device;
predicting the likelihood of platelet aggregation in the blood separation device based at least in part on the determined amount of platelets; and
adjusting an operational parameter if the predicted likelihood of platelet aggregation in the blood separation device approaches, meets, or exceeds a predetermined value.

2. The method of claim 1, wherein said adjusting an operational parameter includes conveying an amount of anticoagulant into the blood and/or the blood separation device.

3. The method of claim 1, further comprising continuously adding anticoagulant to the blood at an anticoagulant flow rate, wherein said adjusting an operational parameter includes adding anticoagulant to the blood at a different anticoagulant flow rate.

4. The method of claim 1, further comprising continuously adding anticoagulant to the blood at an anticoagulant flow rate, wherein said adjusting an operational parameter includes adding anticoagulant to the blood at an elevated anticoagulant flow rate.

5. The method of claim 1, wherein said conveying blood into a blood separation device includes continuously drawing blood from a blood source at a draw flow rate and adding anticoagulant to the blood, wherein said adjusting an operational parameter includes drawing blood from the blood source at a different draw flow rate.

6. The method of claim 1, wherein said conveying blood into a blood separation device includes continuously drawing blood from a blood source at a draw flow rate and adding anticoagulant to the blood, wherein said adjusting an operational parameter includes drawing blood from the blood source at a decreased draw flow rate.

7. The method of claim 1, wherein said conveying blood into a blood separation device includes continuously drawing blood from a blood source at a draw flow rate and continuously adding anticoagulant to the blood at an anticoagulant flow rate, wherein said adjusting an operational parameter includes drawing blood from the blood source at a decreased draw flow rate and adding anticoagulant to the blood at an elevated anticoagulant flow rate.

8. The method of claim 1, wherein said determining the amount of platelets in the blood and/or in the blood separation device includes optically detecting the amount of platelets in the blood and/or in the blood separation device.

9. The method of claim 1, wherein said determining the amount of platelets in the blood and/or in the blood separation device includes calculating the amount of platelets in the blood and/or in the blood separation device.

10. The method of claim 9, wherein the amount of platelets is calculated as a function of the amount of blood, the platelet concentration of the blood, and/or the mean platelet volume of the blood.

11. The method of claim 1, wherein said adjusting an operational parameter includes the injection of a bolus of anticoagulant into the blood separation device.

12. A blood separation system comprising:
a device adapted for separating a blood component from blood, the device including an inlet for passing fluid thereinto and an outlet for removing fluid therefrom;
a pump system for moving fluid through the system; and
a controller, wherein the controller is programmed to
actuate the pump system to convey blood into the device;
determine the amount of platelets in the blood and/or in the device;
predict the likelihood of platelet aggregation in the device based at least in part on the determined amount of platelets; and
adjust the operation of the pump system if the predicted likelihood of platelet aggregation in the device approaches, meets, or exceeds a predetermined value.

13. The blood separation system of claim 12, further comprising an anticoagulant source, wherein the controller is programmed to adjust the operation of the pump system to convey an amount of anticoagulant from the anticoagulant source into the blood and/or the device if the predicted likelihood of platelet aggregation in the device approaches, meets, or exceeds a predetermined value.

14. The blood separation system of claim 12, further comprising an anticoagulant source, wherein the controller is programmed to
actuate the pump system to continuously add anticoagulant to the blood at an anticoagulant flow rate, and
adjust the operation of the pump system to add anticoagulant to the blood at a different anticoagulant flow rate if the predicted likelihood of platelet aggregation in the device approaches, meets, or exceeds a predetermined value.

15. The blood separation system of claim 12, further comprising an anticoagulant source, wherein the controller is programmed to
actuate the pump system to continuously add anticoagulant to the blood at an anticoagulant flow rate, and adjust the operation of the pump system to add anticoagulant to the blood at an elevated anticoagulant flow rate if the predicted likelihood of platelet aggregation in the device approaches, meets, or exceeds a predetermined value.

16. The blood separation system of claim 12, further comprising an anticoagulant source, wherein the controller is programmed to actuate the pump system to continuously draw blood from a blood source at a draw flow rate, actuate the pump system to add anticoagulant to the blood, and adjust the operation of the pump system to draw blood from the blood source at a different draw flow rate if the predicted likelihood of platelet aggregation in the device approaches, meets, or exceeds a predetermined value.

17. The blood separation system of claim 12, further comprising an anticoagulant source, wherein the controller is programmed to actuate the pump system to continuously draw blood from a blood source at a draw flow rate, actuate the pump system to add anticoagulant to the blood, and adjust the operation of the pump system to draw blood from the blood source at a decreased draw flow rate if the predicted likelihood of platelet aggregation in the device approaches, meets, or exceeds a predetermined value.

18. The blood separation system of claim 12, further comprising an anticoagulant source, wherein the controller is programmed to actuate the pump system to continuously draw blood from a blood source at a draw flow rate, actuate the pump system to continuously add anticoagulant to the blood at an anticoagulant flow rate, and adjust the operation of the pump system to draw blood from the blood source at a decreased draw flow rate and add anticoagulant to the blood at an elevated anticoagulant flow rate if the predicted likelihood of platelet aggregation in the device approaches, meets, or exceeds a predetermined value.

19. The blood separation system of claim 12, further comprising an optical sensor associated with the device, wherein the controller is further programmed to determine the amount of platelets in the blood and/or in the device by actuating the optical sensor.

20. The blood separation system of claim 12, wherein the controller is programmed to determine the amount of platelets in the blood and/or in the device by calculating the amount of platelets in the blood and/or in the blood separation device.

21. The blood separation system of claim 20, wherein the controller is programmed to calculate the amount of platelets as a function of the amount of blood, the platelet concentration of the blood, and/or the mean platelet volume of the blood.

22. The blood separation system of claim 12, wherein the controller is programmed to actuate the pump system to add a bolus of anticoagulant to the blood if the predicted likelihood of platelet aggregation in the device approaches, meets, or exceeds a predetermined value.

* * * * *